(12) United States Patent
Godfrin

(10) Patent No.: US 9,580,739 B2
(45) Date of Patent: *Feb. 28, 2017

(54) TEST FOR PREDICTING NEUTRALIZATION OF ASPARAGINASE ACTIVITY

(71) Applicant: ERYTECH PHARMA, Lyons (FR)

(72) Inventor: Yann Godfrin, Lyons (FR)

(73) Assignee: ERYTECH PHARMA, Lyons (FR)

( * ) Notice: Subject to any disclaimer, the term of this patent is extended or adjusted under 35 U.S.C. 154(b) by 60 days.

This patent is subject to a terminal disclaimer.

(21) Appl. No.: 14/489,556

(22) Filed: Sep. 18, 2014

(65) Prior Publication Data

US 2015/0071894 A1 Mar. 12, 2015

Related U.S. Application Data

(63) Continuation of application No. 13/127,756, filed as application No. PCT/EP2009/064793 on Nov. 6, 2009, now Pat. No. 8,852,880.

(30) Foreign Application Priority Data

Nov. 7, 2008 (FR) ...................................... 08 57604

(51) Int. Cl.
*C12Q 1/34* (2006.01)
*A61K 38/50* (2006.01)

(52) U.S. Cl.
CPC ................. *C12Q 1/34* (2013.01); *A61K 38/50* (2013.01); *C12Y 305/01001* (2013.01); *G01N 2333/982* (2013.01); *G01N 2800/52* (2013.01); *G01N 2800/7028* (2013.01)

(58) Field of Classification Search
None
See application file for complete search history.

*Primary Examiner* — Thomas J Visone
(74) *Attorney, Agent, or Firm* — Stephen J. Weyer, Esq.; Stites & Harbison, PLLC.

(57) ABSTRACT

Method of in vitro measurement of the presence of factors that are able to neutralize asparaginase activity in a sample of blood, plasma, serum or derived medium that may contain asparaginase neutralizing factors, obtained from a patient, comprising mixing of said sample with asparaginase, incubation of said mixture, then measurement of the residual asparaginase activity in the mixture and determination or quantification of the presence of said neutralizing factors. Method for predicting the efficacy of a treatment with asparaginase.

27 Claims, 3 Drawing Sheets

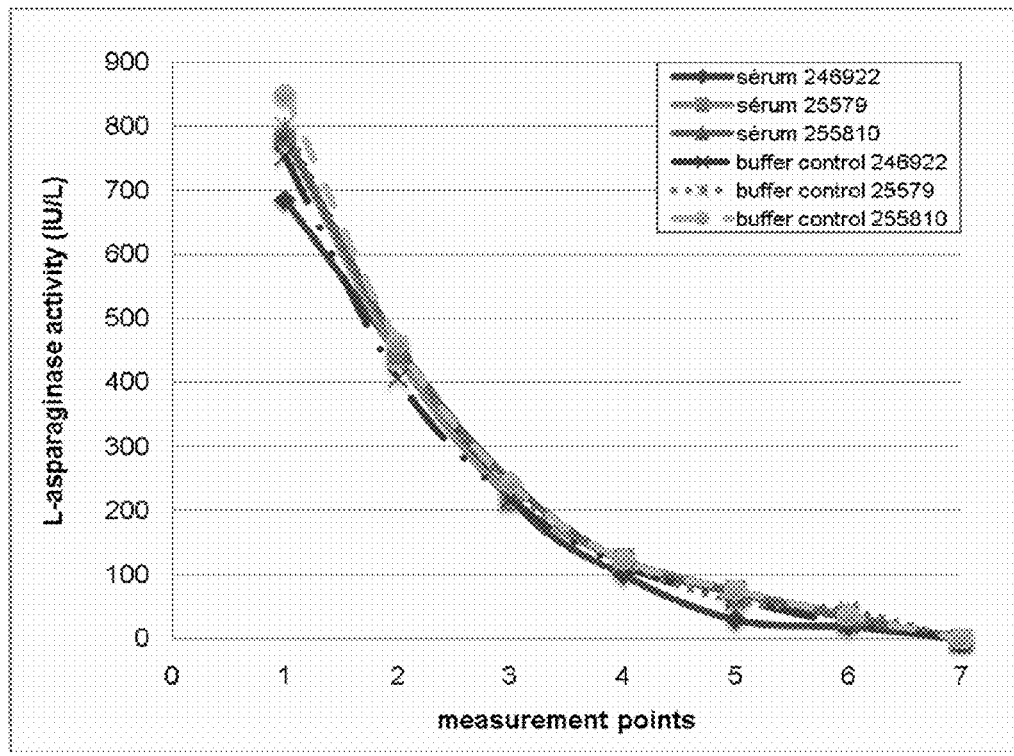
Figure 1: Seven fixed L-asparaginase concentrations (ranging from 0 to 800 IU/L) were measured in three human sera and buffer controls.
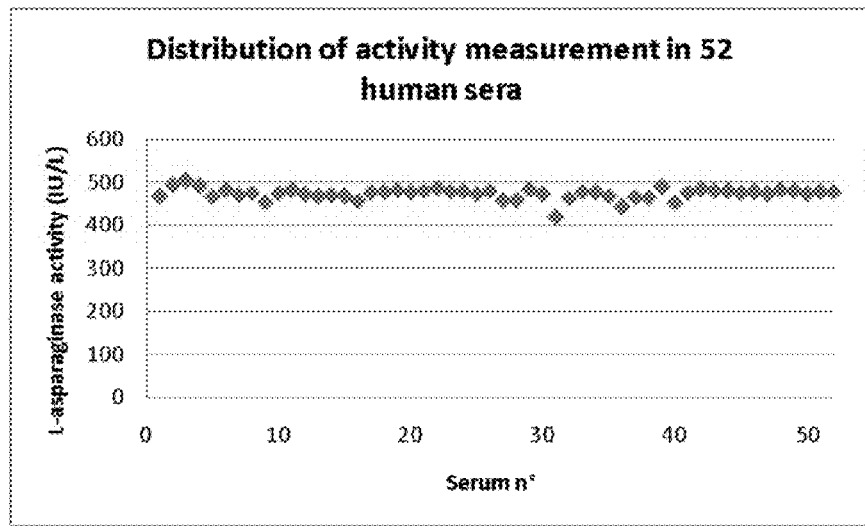
Figure 2: Distribution of activity measured for 52 human sera mixed with L-asparaginase at a final concentration of 500 IU/L

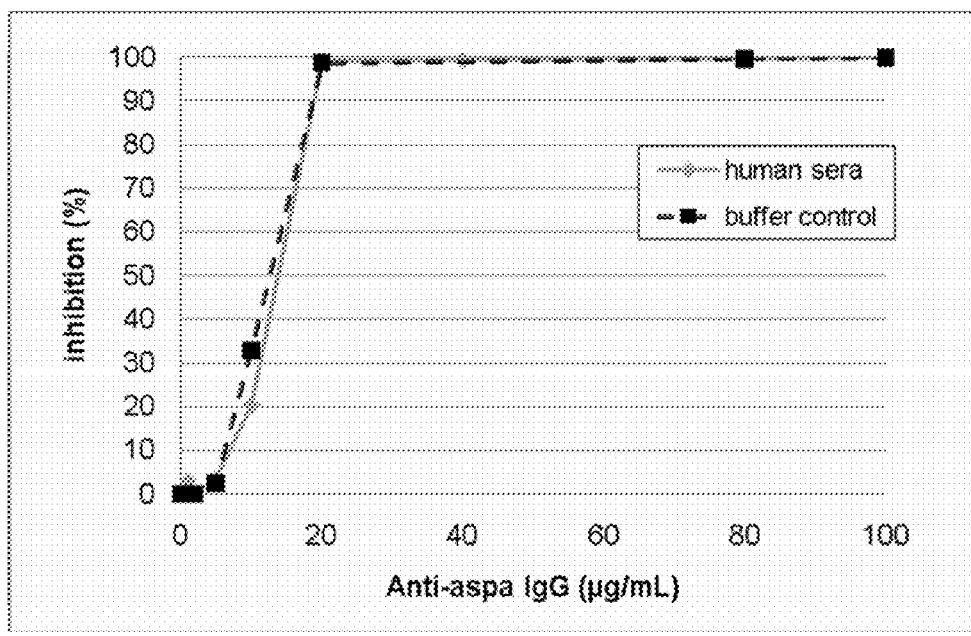
Figure 3 : L-asparaginase activity inhibition versus anti-asparaginase IgG concentration.
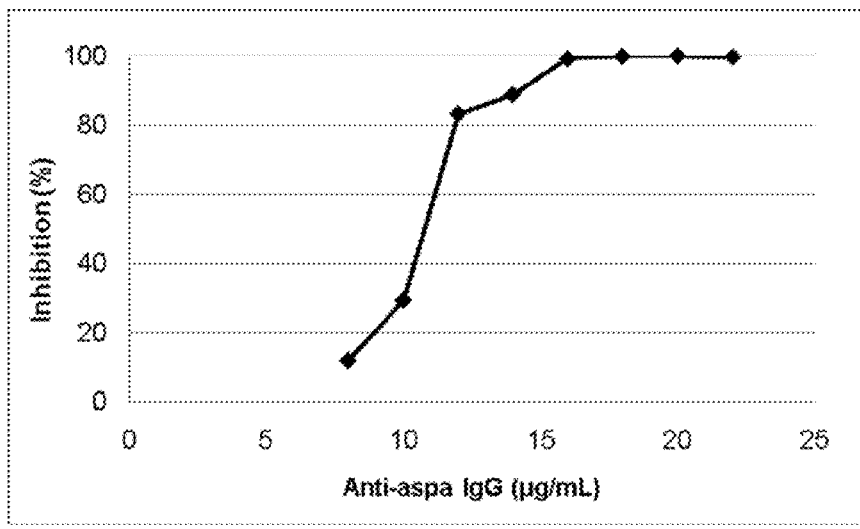
Figure 4 : L-asparaginase activity inhibition versus anti-asparaginase IgG low concentration

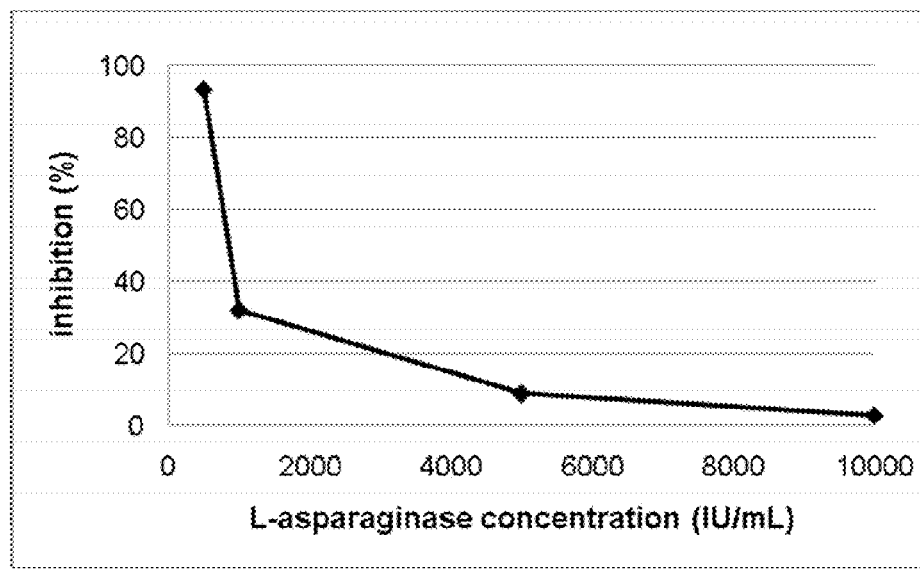
Figure 5 : L-asparaginase activity inhibition versus L-asparaginase concentration
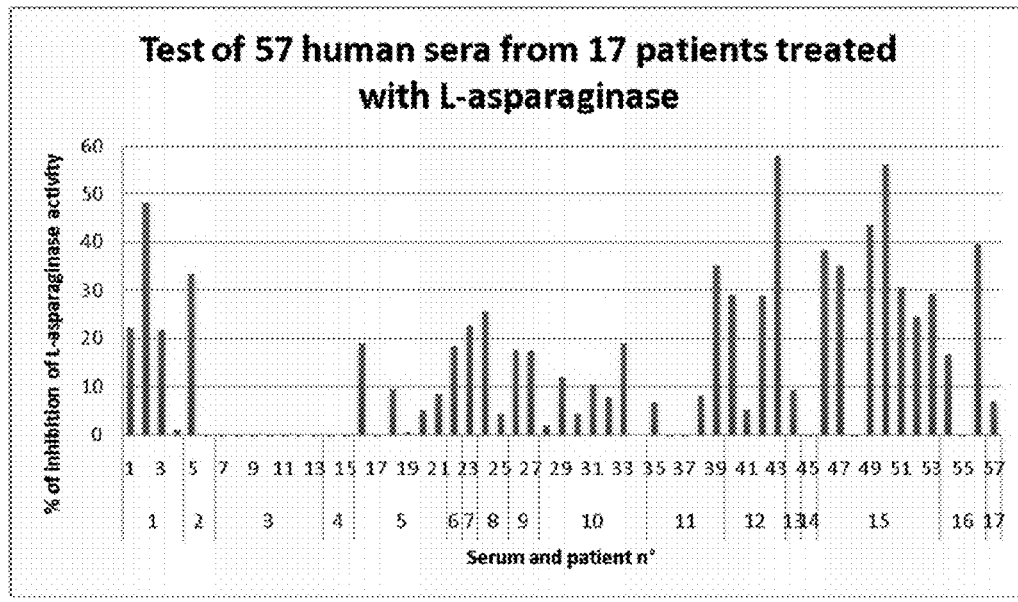
Figure 6: Test of 57 human sera from 17 patients treated with L-asparaginase

TEST FOR PREDICTING NEUTRALIZATION OF ASPARAGINASE ACTIVITY

CROSS-REFERENCE TO RELATED APPLICATION

This application is a continuation application of U.S. patent application Ser. No. 13/127,756, filed Jun. 7, 2011, which is the National Stage of International Application No. PCT/EP2009/064793, filed Nov. 6, 2009, said application herein incorporated by reference.

The invention relates to a test for diagnosing a patient's capacity for responding to treatment with the therapeutic enzyme asparaginase. It notably relates to a test for predicting the efficacy of a treatment using asparaginase in a given patient.

L-asparaginase is an essential component of the chemotherapy protocols that have been used for more than 30 years for the treatment of acute lymphoblastic leukaemias. Its mechanism of action is based on the hydrolysis of the plasma amino acid asparagine, an essential element for tumoral growth of lymphoblasts. In contrast to normal cells, cancerous lymphoblastic cells are unable to produce their asparagine themselves, and are dependent on extracellular sources. Treatment with asparaginase deprives them of this essential constituent and thus brings about their death.

The enzyme produced from microorganisms is currently marketed in three forms: the first two are derived from bacterial sources *Escherichia coli* and *Erwinia chrysanthemi*, the third is obtained by covalent-bond coupling of polyethylene glycol to the native asparaginase of *Escherichia coli* (PEG-asparaginase).

Despite its considerable antileukaemic efficacy, treatment with asparaginase is associated with a certain number of complications connected with the immunogenicity of the enzyme. These complications may be reflected in clinical manifestations or in silent inactivation.

Hypersensitivity reactions, with severity varying from moderate allergic reaction to anaphylactic shock, have been reported by many authors (Wang et al., Journal of Immunological Methods 239 (200) 75-83). Development of reactions of this type, observed with the three forms of asparaginase, generally leads to discontinuation of the treatment for fear of a more severe reaction.

In addition, asparaginase causes the appearance of circulating antibodies that possess neutralizing properties, reflected in an increase in clearance of the enzyme by the reticuloendothelial system and a decrease in its therapeutic efficacy (Müller H. J., Boos J. Crit Rev Oncol/hematol 1998; (28):97-113). These antibodies have been observed with the three forms of the enzyme (*E. coli*, *Erwinia* and PEG-asparaginase), and in this instance the therapeutic objective of asparaginase, which is to achieve rapid and complete depletion of plasma asparagine for an extended period, is not attained.

This inactivation of the enzyme by neutralizing factors, mainly antibodies, present in the patients' serum is not accompanied by clinical signs, it is silent for the clinician.

The inventors have identified that there is therefore a considerable need for clinicians to have at their disposal a test that is quick and is easy to use, for predicting the presence of asparaginase neutralizing factors, mainly antibodies, present in patients' serum. This test would make it possible to adjust the dose of enzyme administered or to replace the asparaginase used with another form of asparaginase that is not sensitive, or is less sensitive, to these neutralizing factors.

Several possibilities were considered for monitoring asparaginase activity in a patient:
Assay of plasma L-asparagine
Assay of plasma L-asparaginase activity
Assay of anti-asparaginase antibodies The level of plasma asparagine is the main biochemical parameter reflecting the therapeutic effect that is desired with asparaginase: a rapid, complete and long-lasting depletion of asparagine. Several methods have consequently been described for its assay. Mostly they are based on combining a stage of separation of the constituents of the sample to be assayed by high-performance liquid chromatography and fluorometric detection or quantification by mass spectrometry. These methods are tedious, they require trained personnel, and their cost and the time taken are incompatible with routine clinical use.

More recently, Verma et al. described a method for rapid assay of asparagine based on the co-immobilization of L-asparaginase and a coloured indicator on various substrates (nitrocellulose membrane, silicone gel or beads of calcium alginate). When one of these supports is brought into contact with a sample of a patient's serum, the immobilized L-asparaginase will degrade the asparagine present. The production of ammonium following this hydrolysis reaction will lead to a colour change of the phenol red indicator. Although this method appears to meet the requirements of simplicity and speed of use, the authors do not supply data by which it can be validated, and there are still doubts about its accuracy.

Apart from the absence of validated methods that can be used easily and quickly, assay of plasma L-asparagine is limited by the following considerations. In vivo, the degradation of asparagine by the action of asparaginase is counterbalanced by the physiological production of asparagine, whereas in vitro, the catalytic effect of the enzyme on asparagine will persist. As a direct consequence, when a serum sample is taken from a patient treated with asparaginase, the presence of a residual amount of enzyme will lead to a bias in measurement of the asparagine level, which will be "falsely" lower than the physiological level (Boos et al., European journal of cancer (1996) 32, 1544-1550). This interference in the analytical procedure results in absence of correlation with the physiological asparaginase activity in the patient tested.

Several methods for assay of plasma L-asparaginase have been described, and that used most often is based on incubation of the serum containing L-asparaginase in a buffer containing L-asparagine, then after stopping the reaction, determination of the ammonium produced using Nessler reagent. Orsonneau et al. proposed a quicker and more accurate automated variant, with which patients treated with L-asparaginase can be monitored (J. L. Orsonneau et al. Ann Biol Clin 2004, 62: 568-72). This method is based on the action of glutamate dehydrogenase, which uses the ammonium produced during the hydrolysis of L-asparagine by L-asparaginase to convert α-ketoglutarate to glutamic acid.

Glutamate Dehydrogenase $$\alpha\text{-ketoglutarate} + NH_4^+ + NADPH \rightarrow L\text{-glutamate} + NADP + H_2O$$

In this reaction, the amount of NADPH oxidized in the course of the reaction is equivalent to the amount of ammonia contained in the sample and can be determined by measuring the decrease in optical density. The kinetics of appearance of ammonium can thus be monitored and the activity of the L-asparaginase can be calculated. Although this method makes it possible to monitor the L-asparaginase activity in a patient, it does not give any predictive information regarding the neutralization of this enzyme by factors present in the serum.

Wang et al. developed a standardized ELISA test for quantifying anti-asparaginase IgGs in plasma samples from patients (B. Wang et al., Journal of Immunological Methods 239 (2000) 75-83). This test was used within the scope of a clinical study for measuring the concentration of anti-asparaginase antibodies present in the serum of patients with acute lymphoblastic leukaemia, treated with L-asparaginase and who did or did not develop an allergic reaction (M. H. Woo et al., Leukemia (1998) 12, 1527-1533). The authors were able to show that the median concentration of anti-asparaginase antibodies was higher in the patients who developed an allergic reaction regardless of whether the measurement is carried out before or after said reaction has occurred. They conclude that there is a benefit in clinical practice of using such a test for predicting the future development of an allergic reaction.

Nevertheless, the predictive value of such a test can be questioned; the ranges of variation of the concentration of anti-asparaginase antibodies measured before the development of an allergic reaction overlap, they are respectively:

from 0.001 to 0.375 unit of OD for the patients who developed an allergic reaction subsequently;

from 0.004 to 0.064 unit of OD for the patients who did not develop a subsequent allergic reaction Moreover, measurement of the concentration of antibodies does not give any information regarding the pharmacological activity of asparaginase in the patient and its possible neutralization by factors present in the serum.

E. H. Panosyan et al., J. Pediatr. Hematol. Oncol. 2004, 26, 4: 217-226 investigated the anti-asparaginase antibody and Asparaginase enzymatic activity in the sera of patients. The authors describe an ex vivo neutralization assay conducted using patient's serum specimens as a source of anti-asparaginase antibodies. The serum specimens were incubated with native or PEG-asparaginase antigen solutions and the remaining asparaginase enzymatic activity was measured. The authors finally recommended the standard monitoring of serum anti-asparaginase antibodies in clinical settings.

The aim of the present invention is therefore to propose a novel approach that makes it possible to overcome the drawbacks of the prior art and to know at a given moment whether a patient has factors that can neutralize asparaginase activity. The method must have the advantage of being completely predictive, i.e. it must not require a stage of administration of the enzyme to the patient to be diagnosed. It must reflect the patient's capacity for responding to any form of asparaginase. Thus, the patient may be a patient who has to be treated for the first time using the enzyme, or a patient who has been treated or is currently being treated with asparaginase. It is possible to test for the presence of factors that can neutralize the activity of the enzyme used for previous or current treatment, which makes it possible to know whether the treatment with this enzyme can be resumed or continued, and optionally adjusted. It is also possible to detect the presence of factors that can neutralize the activity of the enzyme considered for the treatment of said patient, which makes it possible to validate or rule out the use of a particular enzyme.

This knowledge will provide the practitioner with far more pertinent guidance, than with the methods of the prior art, on the form of treatment (posology, dosage regimen) or on the choice of enzyme or its form of administration. Either the neutralizing factors are absent or are present at a low enough level for treatment by means of the test enzyme to be possible, optionally with strengthening of the dosage or of the dosage regimen. Or the neutralizing factors are present at a level that is too high for such a treatment to be continued or initiated, and then the invention makes it possible to test and/or recommend an alternative solution using another form of the enzyme or a form that is less sensitive or is not sensitive to the neutralizing factors, such as the enzyme included in a biovector.

The invention thus aims to propose an in vitro method of determination of the presence of factors that neutralize asparaginase activity in a blood sample from a patient.

It also aims to propose a method for in vitro determination of a patient's capacity for responding (i) positively to treatment with an asparaginase or (ii) of not responding to it or (iii) only responding incompletely.

It also aims to propose a method for predicting the efficacy of a treatment using asparaginase or the fact that this enzyme will not immediately be the object of substantial inactivation of its activity by neutralizing factors.

The invention therefore relates to a method for predicting whether an asparaginase can be active in a patient, wherein one measures in vitro the presence of factors that neutralize asparaginase activity in a sample of blood, plasma, serum or derived medium that may contain said neutralizing factors, obtained from said patient.

The invention relates to a method of in vitro measurement of the presence of factors that neutralize asparaginase activity in a sample of blood, plasma, serum or derived medium that may contain said neutralizing factors, obtained from a patient, comprising mixing of said sample with an asparaginase, incubation of said mixture, then measurement of the residual activity of this asparaginase in the mixture, which reflects and makes it possible to determine and quantify the presence of neutralizing factors in the sample and therefore in vivo in the patient. The method makes it possible to diagnose, qualitatively and quantitatively, the presence of asparaginase neutralizing factors in a patient. By neutralizing factors, it is intended not only anti-asparaginase antibodies, but also any other factor that may inhibit asparaginase or its enzymatic activity, for example proteases such as human asparaginyl endopeptidase.

The invention further relates to a method for predicting whether a given asparaginase can be active in a given patient. This method comprises the determination in vitro of a patient's capacity for responding to treatment with an asparaginase, in which a sample of blood, plasma, serum or derived medium that may contain factors that neutralize asparaginase activity, obtained from said patient, is submitted to the method comprising mixing of said sample with said asparaginase, incubation of said mixture, then measurement of the residual enzymatic activity of said asparaginase in the mixture, which reflects and makes it possible to determine and quantify the presence of neutralizing factors in the sample and therefore in vivo in the patient, that are able to neutralize asparaginase activity, and therefore the patient's capacity to respond to treatment with this enzyme. The invention therefore offers a method for testing the efficacy of an asparaginase for a particular patient.

Depending on the presence or absence of neutralizing factors, and optionally on their level, the process and the method make it possible to determine whether the patient is likely to (i) respond positively to treatment with asparaginase or (ii) not respond to it or (iii) only respond incompletely.

The sample can come from a patient currently being treated with an asparaginase or from a patient who has been treated with an asparaginase.

The sample can also come from a patient who has never been treated with an asparaginase or with this asparaginase.

The asparaginase used in the test can be the one that is being or was used in the treatment carried out on the patient.

It can also be an enzyme from a different source that we wish to test in the patient to predict its efficacy. It is also possible to test various enzymes simultaneously or successively to determine the most suitable treatment for the patient.

The invention therefore provides a method for predicting the efficacy of a treatment with asparaginase or for predicting the fact that this enzyme will not immediately undergo substantial inactivation by neutralizing factors.

The invention applies to all forms of asparaginase, for example L-asparaginase. Without being limited to them, we may mention the native enzymes obtained from any bacterial source, for example L-asparaginase produced by *E. coli*, the enzyme produced by *Erwinia*, mutated enzymes or modified enzymes, for example the pegylated enzymes (PEG-asparaginase). The enzyme can also be of natural, synthetic or recombinant origin. It can be free or included in a biovector, for example in erythrocytes.

The residual activity of the asparaginase in the mixture can be measured by adding, to said mixture, asparagine, preferably L-asparagine and a reagent system that is able to detect the enzymatic degradation of asparagine by active asparaginase.

According to an advantageous configuration, the method comprises the following stages:
(a) incubation of the sample with a known amount of asparaginase;
(b) incubation of the aforesaid mixture with a known amount of asparagine, preferably in an amount causing saturation relative to the amount of asparaginase;
(c) incubation of the aforesaid mixture with the reagent system that can provide assay of the residual enzymatic activity;
(d) qualitative or quantitative evaluation of the loss or retention of enzymatic activity, which correlates with the presence or the content in the sample, of factors that neutralize asparaginase activity.

The incubation in stage (a) takes notably from 1 to 60 min. The enzyme content is notably from 0.1 to 5 IU/ml.

It may be useful and advantageous to inactivate or remove any trace of active enzyme in the test sample. Thus, according to one characteristic, before stage (a), a stage ($a_0$) of removal or inactivation of any asparaginase present in the sample is carried out.

As a variant, before stage (a) it is possible to carry out a stage ($a_0$) of measurement of the baseline asparaginase content of the sample, which makes it possible either to verify that said activity is zero or negligible, or to subtract said activity from that measured by the method.

As a variant, knowing the half-life of the enzyme administered to the patient before the test, we can wait the necessary time between the last administration and taking the blood sample.

According to a particular embodiment, stage (a) is followed by a stage ($a_1$) of removal of the antibody-asparaginase immune complexes. Said removal can be effected easily by centrifugation, so that the mixture involved in stage (b) is the supernatant. Preferably, centrifugation is carried out at 3000-25000 g for between 1 and 30 min at the specified speed.

According to one characteristic, the reagent system is sensitive to the appearance of the ammonium ion resulting from the enzymatic degradation of asparagine by asparaginase. Thus, the presence of neutralizing factors can be determined or measured by carrying out a reaction that consumes the ammonium ion quantitatively. Said consumption of the ammonium ion can be followed, advantageously quantitatively, by measurement of the decrease in optical density (absorbance) of the mixture. Notably the following reactions are carried out:

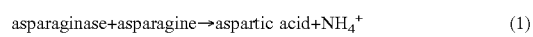
$$\text{asparaginase} + \text{asparagine} \rightarrow \text{aspartic acid} + NH_4^+ \quad (1)$$

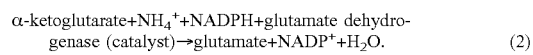
$$\alpha\text{-ketoglutarate} + NH_4^+ + NADPH + \text{glutamate dehydrogenase (catalyst)} \rightarrow \text{glutamate} + NADP^+ + H_2O. \quad (2)$$

Incubation with asparagine is preferably carried out for 2 to 60 min with a saturating amount of asparagine (relative to the amount of enzyme introduced), notably from 10 to 50 mg/ml.

Incubation with the reagent system notably takes from 3 to 20 min.

The invention therefore provides a method for determining whether the patient is likely to (i) respond positively to treatment with an asparaginase or (ii) not respond to it or (iii) only respond incompletely. It therefore makes it possible to confirm or to rule out the possibility of using treatment with the test enzyme, or to make a decision to modify the dosage regimen or to treat the patient using a different asparaginase, notably of a form encapsulated in a biovector.

The invention therefore also relates to a method of treatment of an asparaginase-sensitive pathology in a patient, comprising:
(A) application of the method of determination in vitro of a patient's capacity for responding to treatment with a given form of asparaginase (notably free or modified form), in which a sample of blood, plasma, serum or derived medium that may contain asparaginase neutralizing factors, obtained from said patient, is submitted to the method comprising mixing of said sample with said form of asparaginase, incubation of said mixture, then measurement of the residual activity of asparaginase in the mixture and determination of said neutralizing activity and of the patient's capacity to respond (i) positively to treatment with this form of asparaginase or (ii) not respond to it or (iii) only respond incompletely, and
(B) treatment of the pathology by means of this asparaginase in case (i) or by means of another form of asparaginase in other cases.

According to a preferred embodiment, the other form of asparaginase is asparaginase encapsulated or included in a biovector, notably encapsulated in erythrocytes. Notably they are erythrocytes produced by lysis and resealing, for example according to the teaching of EP 2 377 594.

The pathologies that may benefit from this method include in particular leukaemias, for example acute lymphoblastic leukaemias. We may also mention, without being limited thereto, solid tumours (WO2007/103290), notably pancreatic cancer and ovarian cancer.

The invention will now be described in more detail by means of examples, which illustrate but do not limit the invention.

BRIEF DESCRIPTION OF THE DRAWINGS

The present invention will be described with regard to examples using the Figures as follows:

FIG. 1 is a graph showing effect of patient serum matrix on L-asparaginase activity in which seven fixed L-asparaginase concentrations (ranging from 0 to 800 IU/L were measured in three human sera and buffer controls.

FIG. 2 is a graph showing effect of patient serum matrix on L-asparaginase activity measurement with distribution of activity measured for 52 human sera mixed with L-asparaginase at a final concentration of 500 IU/L.

FIG. 3 is a graph showing L-asparaginase activity inhibition versus anti-asparaginase IgG concentration.

FIG. 4 is a graph showing L-asparaginase activity inhibition versus anti-asparaginase IgG low concentration.

FIG. 5 is a graph showing L-asparaginase activity inhibition versus L-asparaginase concentration.

FIG. 6 is a graph showing % of inhibition of L-asparaginase activity in 57 human sera from 17 patients treated with L-asparaginase.

EXAMPLES

Example 1

Immunization of a Rabbit with L-Asparaginase

A few milliliters of serum are taken from the rabbit before the first immunization so as to have a pre-immune serum. Then the rabbit is injected 4 times with 500 µg of L-asparaginase (Kidrolase®, OPI-EUSA Limonest France). Sera are taken between the first and second immunization and between the second and third immunization. Finally, after the last immunization, the total serum is recovered and stored at −20° C. The final serum is characterized according to its total protein concentration (Biuret method) and its total immunoglobulin concentration.

Example 2

Purification of Rabbit Total IgGs

Purification of the rabbit total IgGs from the final serum, containing anti-asparaginase IgGs, is carried out with the Kit pure 1A from Sigma (# PURE1A). Briefly, 2 ml of serum is clarified by centrifugation or filtration on a 0.45 µm filter before purification of the IgGs. Then 4 ml of "binding buffer" is added to the 2 ml of clarified serum. The mixture is passed, then eluted from the column following the protocol recommended by Sigma. So that they can be injected in the animal, the total IgGs are centrifuged in a filtration column with a threshold of 10 000 Dalton in order to replace the elution buffer with PBS.

Example 3a

Measurement of the Inhibition of an Intermediate Serum on the Enzymatic Activity of L-Asparaqinase (Assay of the Mixture)

Assay of the L-asparaginase was carried out according to the protocol published in: Orsonneau et al., "Automatic kinetic assay of plasma L-asparaginase activity in therapeutic monitoring of acute lymphoblastic leukaemias", *Ann Biol Clin*, 62: 568-572.

An intermediate serum (obtained between the first and second immunization) was used first, for elaborating measurement of the inhibition of enzymatic activity. A concentration of 2 IU/ml of L-asparaginase is used. The enzyme is pre-incubated for 15 minutes at 37° C. with several dilutions of serum, then the enzymatic activity is measured in the mixture. The results are presented in Table 1:

TABLE 1

| Tube No. | L-asparaginase added (IU/ml) | Serum dilution | L-asparaginase in the mixture (IU/ml) | Residual activity, % |
|---|---|---|---|---|
| 1 | 2 | — | 1.96 | 100 |
| 2 | 2 | 1.11 | 0.72 | 36.43 |
| 3 | 2 | ½ | 0.78 | 39.63 |
| 4 | 2 | ¼ | 0.85 | 43.04 |
| 5 | 2 | 1/16 | 1.18 | 60.16 |
| 6 | 2 | 1/32 | 1.29 | 65.91 |
| 7 | 2 | 1/128 | 1.64 | 83.74 |

Table 1 summarizes the measurements of residual enzymatic activities of L-asparaginase in the mixtures (tubes 2 to 7). The rabbit serum inhibits the enzymatic activity of L-asparaginase: the greater the dilution of the serum, the weaker the inhibition.

Tube 1 constitutes a control, showing that incubation of the enzyme alone at 37° C. for 15 minutes does not affect its enzymatic activity.

Example 3b

Measurement of the Inhibition of an Intermediate Serum on the Enzymatic Activity of L-Asparaqinase (Assay of a Supernatant)

An intermediate serum (obtained between the first and second immunization) was used.

In order to simulate phagocytosis of the antigen-antibody complexes by the reticuloendothelial system, the L-asparaginase/serum mixture is incubated for 15 minutes at 37° C., then centrifuged for 10 minutes at 17500 g at 4° C. in order to remove the immune complexes. The enzymatic activity is assayed in the supernatant. The assay results are presented in Table 2:

TABLE 2

| Tube No. | L-asparaginase added (IU/ml) | Serum dilution | L-asparaginase in supernatant (IU/ml) | Residual activity in supernatant (%) |
|---|---|---|---|---|
| 1 | 2 | — | 1.91 | 95.63 |
| 2 | 2 | 1.11 | 0.21 | 10.39 |
| 3 | 2 | ½ | 0.14 | 6.77 |
| 4 | 2 | ¼ | 0.05 | 2.72 |
| 5 | 2 | 1/16 | 0.03 | 1.53 |
| 6 | 2 | 1/32 | 0.02 | 0.98 |
| 7 | 2 | 1/128 | 0.02 | 1.00 |
| control | 2 | pre-immune | 1.82 | 90.81 |

A control, replacing the serum with the pre-immune serum, was added so as to test the specificity of the interaction between L-asparaginase and the anti-asparaginase antibodies present in the serum. This demonstrates that more than 90% of the enzyme is not involved in interaction with nonspecific antibodies.

The antibodies present in the serum interacted with all of the enzyme for the dilutions ¼, 1/16, 1/32 and 1/128.

Example 4

Measurement of Inhibition of the Rabbit Total IgGs from the Enzymatic Activity of L-Asparaginase The same experiment as that presented in Example 3b was carried out with the rabbit total IgGs and a concentration of 1.25 IU/ml of L-asparaginase. The results are presented in Table 3:

TABLE 3

| Tube No. | L-asparaginase added (IU/ml) | Dilution of the IgGs | L-asparaginase in supernatant (IU/ml) | Residual activity in supernatant (%) |
|---|---|---|---|---|
| control | 1.25 | — | 1.19 | 94.99 |
| 1 | 1.25 | — | 1.26 | 100.00 |
| 2 | — | 1/8 | 0.02 | 1.38 |
| 3 | 1.25 | 1/8 | 0.02 | 1.52 |
| 4 | 1.25 | 1/16 | 0.01 | 0.40 |
| 5 | 1.25 | 1/32 | 0.01 | 0.62 |
| 6 | 1.25 | 1/64 | 0.01 | 0.98 |

The rabbit total IgGs, containing anti-asparaginase IgGs, interact with L-asparaginase starting from the dilution 1/64 and cause total inhibition of the enzymatic activity (99.02% of enzyme precipitated).

Example 5

Inactivation, by the Rabbit Total IgGs, of Free L-Asparaqinase Injected in the Mouse An experiment was set up for the mouse (16 mice) to investigate the inhibition of L-asparaginase by the anti-asparaginase IgGs in vivo.

The experimental conditions were as follows:
dose of 100 IU/kg of L-asparaginase, equivalent to 1.25 IU/ml circulating in a 25 g mouse
injection of 7.5 µg of rabbit total IgGs.

Injection of the IgGs or of PBS is carried out 20 minutes before injection of L-asparaginase, free or encapsulated in mouse red blood cells (Asp-RBC). Then 6 hours after this last-mentioned injection, the mice are sacrificed and the blood is collected.

The L-asparaginase activity is then assayed in the plasma and in the RBCs. Table 4 summarizes the values obtained:

TABLE 4

| | | L-asparaginase activity (IU/ml) | |
|---|---|---|---|
| | | IgGs | PBS |
| Asp-RBC | Red blood cells | 0.798 ± 0.126 | 0.879 ± 0.146 |
| | Plasma | 0.013 ± 0.002 | 0.126 ± 0.029 |
| Free L-asparaginase | Red blood cells | 0.132 ± 0.019 | 0.098 ± 0.013 |
| | Plasma | 0.002 ± 0.002 | 0.417 ± 0.103 |

Assay of L-asparaginase in the RBCs of mice that received the Asp-RBCs detects 0.798 and 0.879 IU/ml in the presence of IgGs or of PBS respectively. Therefore the IgGs present in the plasma did not have an inhibitory effect on the encapsulated enzyme. In the plasma of these same mice, free L-asparaginase injected with the Asp-RBCs (there is still in fact a small amount of free enzyme outside of the RBCs, of the order of 10% of the dose) is inhibited in the presence of the IgGs (0.013 IU/ml) and remains active in the presence of PBS (0.126 IU/ml).

When free L-asparaginase was injected, the IgGs inhibited its activity (0.002 IU/ml) whereas injection of PBS had no effect on the activity of the enzyme (0.417 IU/ml). Taking into account the half-life of free L-asparaginase (10 hours), the measurement of 0.417 IU/ml of plasma L-asparaginase corresponds to the residual activity of the free enzyme 6 hours after its injection.

The plasma concentration of L-asparagine was measured in the plasma of 14 of the mice in the study (two could not be used as the volume was too small). The results are presented in Table 5.

TABLE 5

| | Plasma L-asparagine (µmol/litre) | |
|---|---|---|
| | IgGs | PBS |
| Asp-RBC | <2 | <2 |
| Free L-asparaginase | 28.09 ± 3.63 | <2 |

The depletion of L-asparagine was total when the mice were treated with Asp-RBCs or when they received free L-asparaginase in the presence of PBS.

Only the mice treated with free L-asparaginase in the presence of IgG have a plasma concentration of L-Asparagine of 28.09 µM. The enzyme was therefore inhibited in the plasma by the IgGs.

Example 6

Measurement of the Inhibition of Rabbit Total IgGs on the Enzymatic Activity of PEG-Asparaginase Rabbit total IgGs, containing anti-asparaginase IgGs, were tested on PEG-asparaginase (Sigma # A5336). The same experiment as that presented in Example 4 was carried out with the PEG-asparaginase. The results are presented in Table 6.

TABLE 6

| Tube No. | PEG-Aspa added (IU/ml) | Dilution of the IgGs | PEG-Aspa assayed (IU/ml) | Residual activity in supernatant (%) |
|---|---|---|---|---|
| 1 | 0.40 | — | 0.360 | 90.00 |
| 2 | 0.79 | 1/8 | 0.023 | 2.97 |
| 3 | 0.79 | 1/16 | 0.026 | 3.32 |
| 4 | 0.79 | 1/32 | 0.023 | 2.90 |
| 5 | 0.79 | 1/64 | 0.029 | 3.67 |

The rabbit IgGs containing anti-asparaginase IgGs interacted with the PEG-asparaginase. The activity detected in the supernatant is less than 4% of the initial mixed activity with the IgGs.

Example 7

Test Protocol

This protocol applies to a patient who is being considered for treatment with a particular asparaginase. A small blood sample is taken from this patient and is treated conventionally to obtain a serum sample.

Then the following procedure is followed:
($a_0$) optionally inactivation or removal of any asparaginase present in the serum sample, or measurement of the residual enzymatic activity
(a) incubation of the sample with 0.1 to 5 IU/ml of asparaginase for 1 to 60 min;
($a_1$) optionally removal of the immune complexes, preferably by centrifugation at 3000-25000 g for 1 to 30 min at the specified speed;
(b) incubation of the mixture from (a) or of the supernatant from ($a_1$) for 2 to 60 min with a saturating amount of asparagine, notably from 10 to 50 mg/ml;
(c) incubation, notably for 3 to 20 min, of the preceding mixture with the reagent system (α-ketoglutarate, NADPH, glutamate dehydrogenase) that is able to detect the residual enzymatic activity;

(d) qualitative or quantitative evaluation of the loss or retention of enzymatic activity, which correlates with the presence or the content of asparaginase neutralizing factors in the sample.

It is possible to determine levels or thresholds of levels of residual enzymatic activity depending on whether or not stage ($a_1$) is included.

In a patient who has already been treated, if the method shows marked presence of neutralizing factors, a replacement treatment using a different form of asparaginase is recommended and applied. Notably, when the free or modified form is likely to be inhibited, the enzyme encapsulated in erythrocytes is recommended.

The same protocol is applicable simply for testing the potential efficacy of an asparaginase in the patient.

Example 8

Effect of Patient Serum Matrix on L-Asparaginase Activity Measurement

Three human sera, naïve to L-asparaginase treatment, were mixed with 7 L-asparaginase concentrations (from 0 to 800 IU/L) to ensure that human serum has no interference on L-asparaginase activity measurement. Samples were incubated 15 minutes at 37° C. and were centrifuged 10 minutes at 17500 g at 4° C. L-asparaginase activity is checked in the supernatant. As a control, buffer 1×PBS 4% BSA was mixed with the same L-asparaginase concentrations. Results are presented in Table 7.

TABLE 7

| condition | Added L-asparaginase IU/L | Measured L-asparaginase activity (IU/L) | | |
|---|---|---|---|---|
| | | sérum 246922 | sérum 25579 | sérum 255810 |
| pure serum | 800 | 685 | 783 | 788 |
| | 400 | ND* | 442 | 461 |
| | 200 | 220 | 220 | 246 |
| | 100 | 101 | 125 | 122 |
| | 50 | 30 | 76 | 72 |
| | 25 | 19 | 37 | 33 |
| | 0 | 0 | 0 | 3 |
| buffer control | 800 | 753 | 802 | 851 |
| | 400 | 407 | 455 | 463 |
| | 200 | 218 | 236 | 244 |
| | 100 | 115 | 120 | 124 |
| | 50 | 63 | 59 | 77 |
| | 25 | 24 | 45 | 37 |
| | 0 | 0 | — | 0 |

*Not Determined

No interference of human serum was observed on L-asparaginase activity measurement (compared with buffer control: see Table 7 and FIG. 1).

Example 9

Effect of Patient Serum Matrix on L-Asparaginase Activity Measurement and Determination of Basal Activity of Human Serum Fifty-two human sera, naïve to L-asparaginase treatment, were mixed with L-asparaginase at a final concentration of 500 IU/L to ensure that human serum has no interference on L-asparaginase activity measurement. Samples were incubated 15 minutes at 37° C. and were centrifuged 10 minutes at 17500 g at 4° C. L-asparaginase activity is checked in the supernatant. As a control, buffer 1×PBS 4% BSA was mixed with the same L-asparaginase final concentration. Results are presented in Table 8 and in FIG. 2.

TABLE 8

Measurement of l-asparaginase activity on 52 human sera with L-asparaginase added at a final concentration of 500 (IU/L)

| Serum | Measured L-asparaginase activity (IU/L) |
|---|---|
| 1 | 467 |
| 2 | 493 |
| 3 | 505 |
| 4 | 492 |
| 5 | 466 |
| 6 | 482 |
| 7 | 470 |
| 8 | 474 |
| 9 | 453 |
| 10 | 474 |
| 11 | 482 |
| 12 | 472 |
| 13 | 467 |
| 14 | 469 |
| 15 | 468 |
| 16 | 456 |
| 17 | 476 |
| 18 | 477 |
| 19 | 481 |
| 20 | 477 |
| 21 | 479 |
| 22 | 486 |
| 23 | 478 |
| 24 | 479 |
| 25 | 472 |
| 26 | 479 |
| 27 | 457 |
| 28 | 457 |
| 29 | 483 |
| 30 | 472 |
| 31 | 418 |
| 32 | 462 |
| 33 | 477 |
| 34 | 477 |
| 35 | 467 |
| 36 | 442 |
| 37 | 464 |
| 38 | 464 |
| 39 | 489 |
| 40 | 452 |
| 41 | 475 |
| 42 | 484 |
| 43 | 480 |
| 44 | 480 |
| 45 | 475 |
| 46 | 478 |
| 47 | 473 |
| 48 | 482 |
| 49 | 480 |
| 50 | 473 |
| 51 | 478 |
| 52 | 477 |
| Control | 480 |
| Mean | 473.02 |
| Standard deviation | 13.4 |
| Mean − 2SD | 446.22 |
| Mean + 2SD | 499.82 |

The mean activity measured for the 52 human sera is 473 IU/L the standard deviation (SD) is 13.4 IU/L. The mean activity measured for the sera is not significantly different from the control activity. All values are comprised within an acceptable range: on the 52 measurements only 3 are outside the confidence range of [mean−2SD; mean+2SD]. The distribution of the activity measured according to the serum assayed indicate that L-asparaginase activity is not affected by the matrix serum (FIG. 2).

To check the absence of enzymatic activity signal in human serum: 25 human sera naïve to L-asparaginase treatment were assayed for l-asapraginase activity.

TABLE 9

Measurement of l-asparaginase activity on 25 human sera naïve to L-asparaginase treatment

| Serum | Measured L-asparaginase activity (IU/L) |
|---|---|
| 1 | 0 |
| 2 | 2 |
| 3 | 2 |
| 4 | 1 |
| 5 | 2 |
| 6 | 0 |
| 7 | 0 |
| 8 | 0 |
| 9 | 0 |
| 10 | 0 |
| 11 | 0 |
| 12 | 0 |
| 13 | 0 |
| 14 | 1 |
| 15 | 2 |
| 16 | 1 |
| 17 | 5 |
| 18 | 2 |
| 19 | 0 |
| 20 | 3 |
| 21 | 1 |
| 22 | 0 |
| 23 | 0 |
| 24 | 0 |
| 25 | 0 |
| Mean | 0.88 |
| Standard Deviation | 1.27 |

With each of the 25 human sera assayed the L-asparaginase activity is closed to zero. The mean activity measured is 0.88 IU/L and the standard deviation is 1.27 IU/L. The maximum activity measured is 5 IU/L for serum 17 this basal activity signal is not likely to affect the measurement of L-asparaginase activity as it represents 1% of the activity measured for sera mixed with L-asparaginase at a final concentration of 500 IU/L.

Example 10

Inhibition of L-Asparaginase Activity by Anti-Asparaginase IgG Spiked Human Sera Two human sera, naïve to L-asparaginase treatment, were pooled and spiked with anti-asparaginase IgG concentrations ranging between 1 and 100 µg/mL (1, 2, 5, 10, 20, 40, 80, 100 µg/mL). The anti-asparaginase IgG were obtained as described in examples 1 and 2.

Then 500 IU/L of L-asparaginase was added. Samples were incubated 15 minutes at 37° C. and were centrifuged 10 minutes at 17500 g at 4° C. Residual L-asparaginase activity was measured in the supernatant. As a control, buffer 1×PBS 4% BSA was used instead of the human sera pool. Results are presented in Table 10 and FIG. 3.

TABLE 10

| | Added control IgG (µg/mL) | Added anti-aspa IgG (µg/mL) | Added L-asparaginase (IU/L) | measured L-asparaginase activity (IU/L) | inhibition (%) |
|---|---|---|---|---|---|
| human serum pool | 100 | | 500 | 589 | 0.00 |
| | 40 | | 500 | 537 | 0.00 |
| | | 0 | 0 | 0 | — |
| | | 0 | 500 | 534 | 0.00 |
| | | 1 | 500 | 518 | 3.00 |
| | | 2 | 500 | 548 | 0.00 |
| | | 5 | 500 | 515 | 3.56 |
| | | 10 | 500 | 426 | 20.22 |
| | | 20 | 500 | 4 | 99.25 |
| | | 40 | 500 | 3 | 99.44 |
| | | 80 | 500 | 1 | 99.81 |
| | | 100 | 500 | 0 | 100.00 |
| buffer control | 100 | | 500 | 558 | 0.00 |
| | 40 | | 500 | 592 | 0.00 |
| | | 0 | 0 | 0 | — |
| | | 0 | 500 | 564 | 0.00 |
| | | 1 | 500 | 595 | 0.00 |
| | | 2 | 500 | 562 | 0.00 |
| | | 5 | 500 | 550 | 2.48 |
| | | 10 | 500 | 378 | 32.98 |
| | | 20 | 500 | 7 | 98.76 |
| | | 40 | 500 | ND* | — |
| | | 80 | 500 | 2 | 99.65 |
| | | 100 | 500 | 0 | 100.00 |

*Not Determined

When L-asparaginase is mixed with increasing concentrations of anti-asparaginase IgG (specific IgG), in human serum or buffer control, total enzymatic activity inhibition occurs at an igG concentration of 20 μg/mL and higher. Partial inhibition occurs when enzyme is mixed with 5 to 20 μg/mL anti-asparaginase IgG. Below 5 μg/mL anti-asparaginase IgG, L-asparaginase activity is not inhibited.

No inhibition is observed when L-asparaginase is incubated with non-specific IgG (see added control IgG in Table 10).

To refine the inhibition reaction of anti-asparaginase IgG concentration between 10 and 20 μg/mL on L-asparaginase activity, an experiment was performed with IgG concentrations ranging from 8 to 22 μg/mL. As usual, L-asparaginase is added to a final concentration of 500 IU/L. All the samples were incubated 15 minutes at 37° C. and were centrifuged 10 minutes at 17500 g at 4° C. Residual L-asparaginase activity is measured in the supernatant. The assay is performed with a human serum pool. Results are presented in Table 11 and FIG. 4.

TABLE 11

| | Added anti-aspa IgG (μg/mL) | Added L-asparaginase (IU/L) | measured L-asparaginase activity (IU/L) | inhibition (%) |
|---|---|---|---|---|
| human serum pool | | | 2 | — |
| | 22 | | 1 | — |
| | | 500 | 580 | — |
| | 8 | 500 | 510 | 12.07 |
| | 10 | 500 | 410 | 29.31 |
| | 12 | 500 | 98 | 83.10 |
| | 14 | 500 | 65 | 88.79 |
| | 16 | 500 | 5 | 99.14 |
| | 18 | 500 | 1 | 99.83 |
| | 20 | 500 | 0 | 100.00 |
| | 22 | 500 | 2 | 99.66 |

Total inhibition of L-asparaginase activity appears at an IgG concentration of 16 μg/mL. Below 16 μg/mL, L-asparaginase activity inhibition is partial.

The opposite reaction was tested: a fixed anti-asparaginase IgG concentration (13.64 μg/mL corresponding to 80% inhibition) was mixed with L-asparaginase concentrations ranging from 500 to 10000 IU/L. Samples were incubated 15 minutes at 37° C. and were centrifuged 10 minutes at 17500 g at 4° C. Residual L-asparaginase activity is measured in the supernatant. Results are shown in Table 12 and FIG. 5.

TABLE 12

| Added anti-aspa IgG (μg/mL) | Added L-asparaginase (IU/L) | measured L-asparaginase activity (IU/L) | inhibition (%) |
|---|---|---|---|
| 13.64 | | 0 | — |
| 13.64 | 500 | 36 | 93.00 |
| 13.64 | 1000 | 716 | 32.00 |
| 13.64 | 5000 | 5010 | 9.00 |
| 13.64 | 10000 | 10780 | 3.00 |
| | 500 | 548 | — |
| | 1000 | 1052 | — |
| | 5000 | 5480 | — |
| | 10000 | 11080 | — |

The more concentrated L-asparaginase is, the less the fixed IgG concentration (13.64 μg/mL) inhibits its activity. A fixed quantity of anti-asparaginase IgG inhibits a fixed quantity of L-asparaginase. Therefore, L-asparaginase activity inhibition is dose-dependent.

Example 11

Test of 57 Human Sera from 17 Patients Treated with L-Asparaginase

To ensure the assay has the ability to quantify the neutralization of asparaginase in a patient: 57 human sera sampled from 17 Acute lymphoblastic leukaemia patients under treatment with L-asparaginase were tested according to the test protocol described in example 7. The samples were taken at different time of treatment course and a measurement of residual L-asparaginase enzyme activity was conducted to verify that this activity is negligible and will not interfere with the test procedure.

The sera were then mixed with L-asparaginase at a final concentration of 500 IU/l and were incubated 15 minutes at room temperature. The L-asparaginase activity was then determined before and after a centrifugation step of 6 minutes at 7800 rpm. As a control, buffer 1×PBS 4% BSA was mixed with L-asparaginase at a final concentration of 500 IU/L. Results are presented in the table 13 below and in FIG. 6.

TABLE 13

Test of 57 human sera from 17 patients under treatment with L-asparaginase

| Patient | Serum | Initial activity (IU/L) | Activity after addition of L-asparaginase (IU/L) | Activity after addition of L-asparaginase and centrifugation (IU/L) | % of inhibition without centrifugation | % of inhibition after centrifugation |
|---|---|---|---|---|---|---|
| Control | | 6 | 655 | 662 | NA | NA |
| 1 | 1 | 2 | 551 | 515 | 15.88 | 22.21 |
| | 2 | 2 | 440 | 342 | 32.82 | 48.34 |
| | 3 | 1 | 559 | 518 | 14.66 | 21.75 |
| | 4 | 2 | 658 | 655 | −0.46 | 1.06 |
| 2 | 5 | 7 | NA | 441 | NA | 33.38 |
| | 6 | 13 | 767 | 727 | −17.1 | −9.82 |
| 3 | 7 | 1 | 706 | 701 | −7.79 | −5.89 |
| | 8 | −2 | 724 | 716 | −10.53 | −8.16 |
| | 9 | 11 | 692 | 731 | −5.65 | −10.42 |
| | 10 | 2 | 680 | 666 | −3.82 | −0.6 |
| | 11 | 1 | 711 | 733 | −8.55 | −10.73 |
| | 12 | 1 | 754 | 711 | −15.11 | −7.4 |
| | 13 | 2 | 726 | 730 | −10.84 | −10.27 |

TABLE 13-continued

Test of 57 human sera from 17 patients under treatment with L-asparaginase

| Patient | Serum | Initial activity (IU/L) | Activity after addition of L-asparaginase (IU/L) | Activity after addition of L-asparaginase and centrifugation (IU/L) | % of inhibition without centrifugation | % of inhibition after centrifugation |
|---|---|---|---|---|---|---|
| 4 | 14 | 2 | 664 | 744 | −1.37 | −12.39 |
|   | 15 | 15 | 804 | 667 | −22.75 | −0.76 |
| Control |   | 6 |   | 636 | NA | NA |
| 5 | 16 | 1 | 690 | 516 | −8.49 | 18.87 |
|   | 17 | 2 | 649 | 678 | −2.04 | −6.6 |
|   | 18 | 2 | 684 | 575 | −7.55 | 9.59 |
|   | 19 | ND | 622 | 633 | 2.2 | 0.47 |
|   | 20 | 1 | 670 | 604 | −5.35 | 5.03 |
|   | 21 | 1 | 609 | 583 | 4.25 | 8.33 |
| 6 | 22 | 1 | 659 | 519 | −3.62 | 18.4 |
| 7 | 23 | 2 | 508 | 492 | 20.13 | 22.64 |
| 8 | 24 | 1 | 761 | 473 | −19.65 | 25.63 |
|   | 25 | 0 | 633 | 608 | 0.47 | 4.4 |
| 9 | 26 | 4 | 705 | 524 | −10.85 | 17.61 |
|   | 27 | 2 | 656 | 525 | −3.14 | 17.45 |
| 10 | 28 | 3 | 608 | 623 | 4.4 | 2.04 |
|   | 29 | 1 | 649 | 560 | −2.04 | 11.95 |
|   | 30 | 3 | 610 | 609 | 4.09 | 4.25 |
|   | 31 | 7 | 694 | 570 | −9.12 | 10.38 |
|   | 32 | −1 | 598 | 586 | 5.97 | 7.86 |
|   | 33 | 2 | 589 | 516 | 7.39 | 18.87 |
|   | 34 | 0 | 527 | NA | 17.14 | NA |
| Control |   | 3 | 661 | 629 | NA | NA |
| 11 | 35 | 2 | 713 | 587 | −7.87 | 6.68 |
|   | 36 | 1 | 499 | 667 | 24.51 | −6.04 |
|   | 37 | 3 | 596 | 666 | 9.83 | −5.88 |
|   | 38 | 2 | 701 | 579 | −6.05 | 7.95 |
|   | 39 | 2 | 850 | 408 | −28.59 | 35.14 |
| 12 | 40 | 2 | 798 | 446 | −20.73 | 29.09 |
|   | 41 | 2 | 599 | 596 | 9.38 | 5.25 |
|   | 42 | 5 | 814 | 448 | −23.15 | 28.78 |
|   | 43 | 3 | 752 | 265 | −13.77 | 57.87 |
| 13 | 44 | 1 | 705 | 570 | −6.66 | 9.38 |
| 14 | 45 | 1 | 685 | 659 | −3.63 | −4.77 |
| 15 | 46 | 1 | 573 | 388 | 13.31 | 38.31 |
|   | 47 | 2 | 492 | 408 | 25.57 | 35.14 |
|   | 48 | 1 | 605 | 678 | 8.47 | −7.79 |
|   | 49 | 2 | 571 | 355 | 13.62 | 43.56 |
|   | 50 | 2 | 725 | 275 | −9.68 | 56.28 |
|   | 51 | 2 | 464 | 437 | 29.8 | 30.52 |
|   | 52 | 3 | 497 | 475 | 24.81 | 24.48 |
|   | 53 | 0 | 540 | 445 | 18.31 | 29.25 |
| 16 | 54 | 3 | 550 | 524 | 16.79 | 16.69 |
|   | 55 | 2 | 568 | 637 | 14.07 | −1.27 |
|   | 56 | 1 | 595 | 379 | 9.98 | 39.75 |
| 17 | 57 | 1 | 709 | 585 | −7.26 | 7 |

ND: Not determined
NA: Not Applicable

All the samples have a residual asparaginase activity which is negligible, the highest residual activity is of 15 IU/L and should not interfere with the test procedure as it represents only 3% of the theoretical added L-asparaginase. The asparaginase activity measured for the control is higher than expected (655, 636 and 661 IU/L respectively for the 3 control compared to the 500 IU/L that were expected). The percentage of inhibition of asparaginase activity was calculated based on enzymatic activity measured for the control. The fact that numerous values of inhibition percentage are negative indicate a bias in the measurement procedure.

The percentage of inhibition of asparaginase activity is higher after centrifugation suggesting that the centrifugation step has eliminated some immune complexes that were formed between asparaginase and anti-asparaginase antibodies.

On the 17 patients assayed 14 experience an inhibition of the asparaginase activity by factors present in their serum (FIG. 6). Height patients have a percentage of inhibition above 20% but only three patients have a percentage of inhibition higher than 40% (FIG. 6).

The invention claimed is:

1. A method of treatment of an asparaginase-sensitive pathology in a patient, said methods comprising:
   (a) obtaining a sample of blood, plasma, or serum from a patient;
   (b) incubating said sample with a known amount of asparaginase for a period of time sufficient to produce antibody-asparaginase immune complexes;
   (c) removing from the incubated sample any antibody-asparaginase immune complexes formed during incubation step (b) and recovering a sample free of antibody-asparaginase immune complexes;
   (d) incubating the sample obtained at step (c) with asparagine;

(e) determining a residual asparaginase activity or the amount of asparaginase residual activity in the resultant mixture of step (d); and (f) treating said patient by means of the asparaginase and/or by means of another form of asparaginase.

2. The method according to claim 1, further comprises wherein the treating said patient of step (f) depends on step (e) determining the residual asparaginase activity or the amount of asparaginase residual activity in the resultant mixture of step (d).

3. The method according to claim 1, further comprises after step (e), determining or quantifying the presence of neutralizing factors.

4. The method according to claim 1, wherein the patient is currently being treated with asparaginase or has been treated with asparaginase.

5. The method according to claim 1, wherein measuring the activity of the asparaginase in the mixture is carried out by adding, to the mixture, asparagine and a reagent system suitable for assaying residual enzymatic activity.

6. The method according to claim 5, comprising the following stages:

(a) incubating the mixture with the reagent system suitable for assaying the residual enzymatic activity; and (b) qualitatively or quantitatively evaluating a loss or retention of enzymatic activity, which is correlated with the presence or with the content of neutralizing factors of said asparaginase in the sample.

7. The method according to claim 1, comprising, before incubating the sample with said form of asparaginase, a step ($a_o$) of removing or inactivating any asparaginase that may be present in the sample.

8. The method according to claim 1, comprising, before incubating the sample with said form of asparaginase, a step ($a_o$) of measuring the baseline content of asparaginase in the sample.

9. The method according to claim 5, wherein the reagent system is sensitive to the appearance of ammonium ions resulting from enzymatic degradation of asparagine by asparaginase.

10. The method according to claim 9, which employs a reaction that consumes the ammoniums ions quantitatively.

11. The method according to claim 10, wherein the quantitative consumption of the ammonium ion is measured by measuring the decrease in optical density of the mixture.

12. The method according to claim 5, which employs the following reactions:

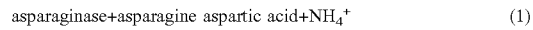

$$\text{asparaginase} + \text{asparagine} \rightarrow \text{aspartic acid} + NH_4^+ \quad (1)$$

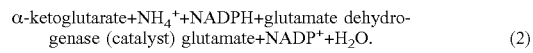

$$\alpha\text{-ketoglutarate} + NH_4^+ + NADPH + \text{glutamate dehydrogenase (catalyst)} \rightarrow \text{glutamate} + NADP^+ + H_2O. \quad (2)$$

13. The method according to claim 1, which comprises determining the patient's capacity to respond: (i) positively to treatment with the asparaginase; (ii) not respond to it; or (iii) only respond incompletely.

14. The method of claim 1, further comprising identifying the asparaginase is active in the patient sample and is able to be effective in the patient if the activity is present.

15. The method according to claim 13, which comprises, for cases (ii) and (iii), treating the patient using a different asparaginase.

16. The method according to claim 13, which comprises, for case (i), treating the patient using the asparaginase.

17. The method according to claim 15, wherein the different asparaginase is an asparaginase included in a biovector.

18. The method according to claim 15, wherein the different asparaginase is an asparaginase included in erythrocytes.

19. The method according to claim 2, wherein another form of asparaginase of step (f) is an asparaginase included in a biovector.

20. The method according to claim 2, wherein another form of asparaginase of step (f) is an asparaginase included in erythrocytes.

21. The method of claim 1, wherein a medium is derived from the sample obtained in step (a) and used in the incubation step (b).

22. The method of claim 14, which comprises modifying the dosage regimen based on identifying the asparaginase is active in the patient sample and is able to be effective in the patient if the activity is present.

23. The method of claim 1, wherein the patient has leukemia.

24. The method of claim 1, wherein the patient has acute lymphoblastic leukemia.

25. The method of claim 1, wherein the patient has a solid tumor.

26. The method of claim 1, wherein the patient has pancreatic cancer.

27. The method of claim 1, wherein the patient has ovarian cancer.

* * * * *